United States Patent [19]

Ekman et al.

[11] Patent Number: 4,931,284

[45] Date of Patent: Jun. 5, 1990

[54] MICRO-CAPSULES

[75] Inventors: Bo M. Ekman, Malmö; Kare V. Larsson, Bjärred; Ake R. Lindahl, Skurup; Ulf S. E. Rothman, Skanör, all of Sweden

[73] Assignee: Biogram AB, Malmo, Sweden

[21] Appl. No.: 74,700

[22] PCT Filed: Oct. 6, 1986

[86] PCT No.: PCT/SE86/00451

§ 371 Date: Jun. 29, 1987

§ 102(e) Date: Jun. 29, 1987

[87] PCT Pub. No.: WO87/02582

PCT Pub. Date: May 7, 1987

[30] Foreign Application Priority Data

Oct. 28, 1985 [SE] Sweden .............................. 8505086

[51] Int. Cl.$^5$ ........................ A61K 37/20; A61K 9/52
[52] U.S. Cl. ..................... 424/450; 264/4.1; 264/4.6; 424/451; 428/402.2; 428/402.24; 514/962; 514/963
[58] Field of Search ............... 424/450, 451; 264/4.1, 264/4.6; 428/402.2, 402.24; 514/962, 963

[56] References Cited

FOREIGN PATENT DOCUMENTS 2249552 5/1973 Fed. Rep. of Germany ...... 424/450
PCT/US84/-
00906 1/1985 PCT Int'l Appl. .

Primary Examiner—Mark L. Bell
Assistant Examiner—Anthony J. Green
Attorney, Agent, or Firm—Jones, Askew & Lunsford

[57] ABSTRACT

The invention relates to a completely novel type of micro-capsules, viz. such capsules where an encapsulated hydrophobic or lipophilic substance is surrounded by polar solid crystals of polar lipids which expose their hydrophilic face outwards and their hydrophobic face turned inwards towards the hydrophobic or lipophilic substance. These micro-capsules can be utilized to encapsulate for instance tacky substances or substances to be protected against oxidation or influence from light. Moreover, an especially interesting use according to the invention is the use of said micro-capsules in an ointment base, where the active ingredient is well protected within said capsules up to the use but which at the application on the skin directly comes into contact with the skin surface as a consequence of the crystalline structure of the shell. Furthermore, the invention relates to a special micro-capsule composition in the form of a dispersion of said micro-capsules in water or a polar liquid, where the crystals constitute 5–50 percent by weight and water or the polar liquid 50–95 percent by weight. Moreover, the invention relates to a process for the preparation of said micro-capsules, wherein a mixture of said polar lipid with water or polar liquid is formed, the mixture is heated above the transition temperature of the lipid and the mixture is then cooled to the desired temperature so as to obtain crystallization, the hydrophobic or hydrophilic substance being added before or during the lipophilic phase. Finally, the invention relates to a crystal dispersion of the polar lipid in a polar liquid, such as glycerol, ethylene- or propylene glycol.

19 Claims, No Drawings

MICRO-CAPSULES

TECHNICAL FIELD

The present invention relates to the field of micro-encapsulation, i.e. the technique by means of which a substance that is intended to be protected from the surrounding or contact with another substance, is encapsulated in a surrounding protecting or contact-preventing envelope or shell. In this context the primary novelty is that it has turned out possible to encapsulate a hydrophobic or lipophilic substance within a crystalline shell of surface active crystals of polar lipids, which as far as we know of has not been previously used and means essential advantages as compared to known micro-encapsulation methods. In addition to an improved effect in several aspects relative to the prior art the invention also opens up possibilities for completely new application areas for micro-capsules, among which the use in ointment bases can be mentioned. More specifically the invention relates to novel micro-capsules, to an especially preferable micro-capsule composition containting said micro-capsules, to a process for the preparation of the micro-capsules or the micro-capsule composition as well as to a novel use of said micro-capsules. Furthermore, according to still another aspect the invention relates to a novel crystal dispersion and a method of preparing the same.

BACKGROUND OF THE INVENTION

Micro-capsules and micro-encapsulation are terms which are well known per se to a person skilled in the art, which means that there should be needed no definitions of said terms here. It is true that the meaning of the terms "micro" may possibly vary from one application area to another, but since the invention is not directly critical in this aspect, i.e. that a very specific size is necessarily referred to, that term should be considered in the present case merely as the conventionally accepted meaning of particles which are not macro particles of the sizes of several millimeters and thereabove. However, the especially preferable micro-encapsulation technique that is claimed generally gives particles having a size below 1 mm, which means that such particles are generally referred to in connection with the present invention.

Especially within the pharmaceutical and food industries there is today a great interest in encapsulating substances for the purpose of reducing the contacts with the surroundings. There are several known methods of performing a micro-encapsulation, such as e.g. a so-called complex coacervation in an aqueous medium, a phase separation, a polymerization in situ and a coating operation. The protective layer or shell is primarily built up from polymers, synthetic or native ones, or from amorphous lipids. For a survey of these different methods reference is made to Biomedical applications of micro-encapsulation; Lim, Franklin; CRC Press (1984). However, said known methods are connected with disadvantages of different kinds. Thus, it may for instance be that the manufacture is performed in the presence of non-physiological or toxic reagents or that the obtained structure is non-stable or non-reproducible.

SUMMARY OF THE INVENTION

The above-mentioned deficiencies and disadvantages are eliminated or at least reduced by means of the present invention. This is primarily accomplished by the use of a completely new type of shell in these connections, viz. a solid crystalline shell from surface active lipids, wherein these expose their hydrophilic face outwardly and their hydrophobic face inwardly towards the hydrophobic or lipophilic substance to be encapsulated. In other words the micro-capsules according to the invention possess a hydrophilic outer surface while at the same time they enclose a hydrophobic or lipophilic substance.

Thus, the characteristic features of the micro-capsules according to the invention are that the substance is a hydrophobic or lipophilic substance and that it is surrounded by surface active solid crystals of polar lipids, i.e. having one hydrophilic and one hydrophobic side or face, said lipids exposing their hydrophilic face outwards and their hydrophobic face turned inwards the towards the hydrophobic or lipophilic substance.

With reference to those lipid crystals which are utilized according to the present invention to obtain micro-capsules it can be mentioned as a background that most amphiphilic substances, such as e.g. lipids, crystallize in bimolecular layers with dominating crystal surfaces parallel to said layers. The crystal surface can either be formed from polar end groups or from methyl end groups. It has previously been possible to prepare crystals which have their both sides consisting of polar groups, i.e. hydrophilic ones, see GB patent specification No. 1,174,672, in which details can be found as concerns the hydrophilic crystals.

Contrary to previous patents the present invention discloses crystals with a hydrophilic and a hydrophobic side or face. The prior art does not disclose that it is possible to obtain by means of such crystals, as is the case with the present invention micro-capsules of the type referred to and even less that such micro-capsules would possess those outstanding properties which the micro-capsules according to the invention have been shown to possess.

In order to show at least to some extent said properties and advantages in connection with the invention the invention will now shortly be described in connection with the preferable method of manufacture thereof. In this context the invention can generally be said to represent a method of manufacturing micro-capsules by means of surface active crystals which are grown around a hydrophobic particle or drop in an aqueous medium or in some other polar liquids so as to form a covering surface layer. The thickness of the covering layer can be varied by means of changes of the composition or an adjustment of the crystallization process. The advantages of the micro-encapsulation according to the invention are that the manufacture can be performed completely in an aqueous medium without the presence of non-physiological reagents, such as cross-linking agents, accelerators and initiators, and that the substances used for the crystals are natural food ingredients, or additives of a GRAS-standard. Other advantages are that partly the crystalline structure is stable, partly it is reproducible, i.e. all layers are of a similar structure. Thus, when using polymers non-ordered amorphous structures are created with for instance varying diffusion rates and risks of transformation phenomena. Furthermore, the micro-capsules according to the invention are easily dispersable in water, which will be described more in detail below.

By means of the micro-capsules according of the invention inter alia the following advantages are obtainable:

Obtain solid particles of oils
Control smell and flavour
Protect the substance from oxidation
Alter solubility and surface properties
Retard evaporation
Prevent incompatibilities
Handle toxic materials
Improve flow properties
Obtain delayed release of an active substance, i.e. so called slow release.

It is true that several of these effects are previously known per se in connection with micro-encapsulation according to the prior art, but as will be clear for instance from the working examples to follow, the encapsulating technique according to the present invention has in many respects turned out to be superior to the prior art. In addition to the fact that the invention enables a completely different reproducibility than according to the prior art, the micro-capsules according to the invention can thus for instance give an essentially improved stability with reference to the encapsulated substance, while they can at the same time make possible a more rapid and more effective release of the active encapsulated substance if desired. This of course represents an extremely valuable contribution to the technique within this field, as said properties have previously been considered more or less incompatible with each other. The reason for the rapid and effective release of the active ingredient in those cases where this is desirable is supposed to be the structure of the crystals, i.e. that at shear, a small temperature raise and/or a contact with hydrophobic surfaces the crystals can be brought to slide away and open a contact path between the encapsulated substance and the surface upon which said substance is to be applied. This special effect will be illustrated more below in connection with the special use according to the invention.

Although the invention is generally applicable to all lipids of the type referred to above, i.e. such lipids which are able to form solid surface active crystals, a preferable embodiment of the invention is represented by the case when the lipid has a temperature for crystallization to a solid phase from a lamellar liquid crystalline phase that is imperative to the operation of the invention, of between ambient temperature (about 20° C.) and about 100° C. Thus, said temperature range is suitable from a manufacturing point of view as well as from a handling point of view.

Especially preferable surface active lipid crystals according to the invention are β-crystals from a monoglyceride of a fatty acid having a chain length of 12–18 carbon atoms or monoglycerol ethers having ether chains of the corresponding chain length or fatty acid esters of ascorbic acid, the fatty acid also in last-mentioned case preferably having a chain length of 12–18 carbon atoms, as these have turned out to give by means of the special process according to the invention surface active solid crystals of the kind referred to. The fatty acids as well as the ethers are preferably saturated ones.

The above-mentioned monoglyceride can be an 1- or 2-monoglyceride, preferable compounds within the above-mentioned group being 1-monolaurin, 1-monoyristin, 1-monopalmitin and 1-monostearin or a mixture of two or more of these. Especially preferable thereof, e.g. in connection with ointment bases, is 1-monolaurin or a mixture of 1-monolaurin and 1-monomyristin wherein the contents of 1-monolaurin is at least 10 percent by weight.

Examples of other polar lipids which should be useful in accordance with the invention are phosphate esters and lactic esters of fatty acids, which preferably also contain 12–18 carbon atoms and are preferably saturated.

As concerns the substance to be encapsulated within the surface active lipid crystals it should be noted that the invention is applicable to each substance of a hydrophobic or lipophilic character. Specific examples of such substances will be given below in connection with certain especially interesting applications of the micro-capsules. In the present case the expressions referred to are used in their general, established meanings, i.e. hydrophobic represents in principle "water-repelling", while lipophilic relates to "lipid attracting" or similar. Furthermore the hydrophobic or lipophilic substance can be in a solid or a liquid aggregation condition, i.e. it can be a liquid, a solution or be represented by particles.

According to an especially interesting embodiment of the invention the hydrophobic or lipophilic substance is selected from the group of substances which are not easily soluble in water and which have a melting temperature or point that is close to or below the intended use temperature of the micro-capsules. Thus in addition to the stabilizing effect that is obtainable by micro-capsules this means that a substance which is tacky per se can be encapsulated to a non-tacky easily handable product. An example of such a substance is coal-tar which is utilized in connection with pharmaceuticals, e.g. in psoriasis preparations.

The lipid crystal encapsulation in accordance with the invention has also been shown to represent an unexpectedly effective way of protecting easily oxidated substances, e.g. lipids present in food stuffs. Food stuffs enriched on essential fatty acid triglycerides, fat-soluble vitamins and porfyrin complexes of mineral substances represent the most important applications, but also spice oils and some lipophilic flavouring agents can be protected in the corresponding way. Examples of specific substances in this application are marine oils, ditranol, A-vitamin and D-vitamin and flavonides of the types catechin, rutin, rotenon, pyretrum or derivatives thereof as well as tanning agents such as for instance tannin.

According to still another preferable embodiment of the invention the hydrophobic or lipophilic substance is selected from the group of light-decomposition-sensitive substances, as the novel crystalline shell according to the invention has also in this case turned out to give an outstanding stability. An example of a light-decomposition-sensitive substance for which the micro-encapsulation technique according to the invention is especially interesting, is a tetracycline.

According to the invention it has also been shown to be possible to prevent in an advantageous way the formation or creation of incompatibilities. By encapsulating a substance in the micro-capsules according to the invention it is thus possible to mix the same with a substance that is generally incompatible therewith, e.g. hydrocortisone with hydrogen peroxide. Micro-capsules from hydrocortisone can be admixed with an aqueous solution of hydrogen peroxide without having any reduction of the stability of the steroide.

As concerns the proportion of the hydrophobic or lipophilic substance in the micro-capsules according to the invention said proportion is not especially critical, but the specific use will be decisive for what concentration is chosen. Thus generally the invention is applicable also to a large amount or proportion of the hydrophobic or lipophilic substance, e.g. in a proportion of up to about 90 percent by weight based on the weight of the micro-capsules. As concerns the lower limit it is imperative only that the proportion of hydrophobic or lipophilic substance is large enough to obtain a homogeneous product. Otherwise, the concentration might be infinitely small.

Apart from the water or the polar liquid which is absorbed by the polar lipid in the formation of the surface active crystals it is possible according to the invention to prepare more or less dry micro-capsules, e.g. by using in the special process claimed a final step for the evaporation of water or polar liquid, e.g. by lyophilization. Thus the term micro-capsules according to the invention represents either a product of a dry nature or a product having varying amounts of liquid. However, an especially preferable micro-capsule composition according to the invention is represented by a dispersion of the previously defined micro-capsules in water or in said polar liquid, wherein the water or the polar liquid constitutes 50-95 percent by weight of the dispersion and the surface active crystals 5-50 percent by weight of the same. Said composition is especially preferable partly for the reason that it is the composition that is directly obtained from the process according to the invention, partly for the reason that such a product has a consistency that is suitable for many different applications.

In connection with the invention the term polar liquid represents another liquid but water and a liquid that is able to produce said surface active crystals from the polar lipids. Examples of polar liquids for use in accordance with the invention are glycerol, propylene glycol and ethylene glycol. Thus, according to the invention it has also unexpectedly turned out that it is not only water that can be used for the preparation of the surface active crystals but also certain types of polar liquids can be utilized for said purpose. This will be illustrated more below.

From the above discussion relating to the proportion of hydrophobic or lipophilic substance in the micro-capsules it can be gathered that said proportion is primarily not either critical in connection with the micro-capsule composition claimed. However, an especially preferable concentration range is 0.1-15 percent by weight based on the weight of the composition.

As was mentioned above the invention also relates to a process for the preparation of the micro-capsules or of a micro-capsule composition in accordance with the above-mentioned definitions. Said process is characterized by mixing the polar lipid with water or said polar liquid to the formation of a mixture having a water or liquid content of 50-95 percent by weight, imparting to said mixture a temperature above the so-called transition temperature of the lipid, which temperature is defined as the lowest temperature at which a particle of the lipid in contact with an excess of water or polar liquid absorbs water or polar liquid respectively, and is transformed to cylindrical or spherical particles having a strong birefringence, which particles are called liposomes, keeping said mixture above said temperature whith stirring until said transformation has occurred, and cooling said mixture with continued stirring to ambient temperature or the desired temperature so as to obtain said surface active solid crystals, the hydrophobic or lipophilic substance being added before the lipid is transformed into liposomes or while it is still in the liposomic form. Dependent on the desired solid contents of the micro-capsules water or polar liquid can then optionally be evaporated if desired.

Thus, the novel micro-encapsulation principle according to the invention is based on the possibility of getting crystals of lipids to expose lipophilic as well as hydrophilic dominating surfaces. GB patent specification No. 1,174,672, referred to above, discloses per se a method of preparing lipid crystals having hydrophilic surfaces, which means that further details concerning the process can be taken from said specification. However, in accordance with the invention it has unexpectedly been shown that by adding the hydrophobic or lipophilic substance before the lipid is transformed into liposomes or while it is still in the liposomic form it is possible to obtain micro-capsules having a completely new structure and with outstanding properties. Thus, it has unexpectedly turned out that it is possible to control the crystallization of a polar lipid so that the leaf-shaped crystals are built up at an interphase between the oil phase and water (or polar liquid) and orient their polar groups outwards towards the water (polar liquid) and the methyl end-groups of their hydrogen tails towards the oil phase. This means that in total the crystals are surface active with a hydrophilic surface towards water (polar liquid) and a hydrophobic surface towards the hydrophobic or lipophilic substance and that last-mentioned substance is surrounded by lipid crystals in such a way that so-called micro-capsules are obtained. Similar proportions between oil, water and other polar lipids, e.g. glycerol monostearate, are disclosed in previously published compositions; see for instance Practical emulsions, Vol. 2, H. Bennet, J-L. Bishop Jr. and M. F. Wulfinghoff, page 37 No. 24, Chemical Publ. Co. New York (1968). In the previously disclosed compositions the polar lipid is dissolved in the oil phase, a monomolecular layer of the polar lipid being formed at the interphase between oil and water, which layer acts as a barrier against the formation of the lamellar liquid crystalline phase that is formed in accordance with the present invention. Comparative tests between known compositions and the novel composition according to the invention show that well-defined crystalline layers of the polar lipid at the interphase oil-water are formed only at the process according to the present invention.

Thus, the prerequisite of a manufacture of encapsulated oil phase or of encapsulated lipophilic particles in a water-medium by means of lipid crystals is that a lamellar liquid crystalline phase of the lipid referred to is created in water. How such a liquid crystalline phase can be created or formed is disclosed more in detail also in Liquid crystallinity in lipid-water systems, Krister Fontell, Mol. Cryst. Liq. Cryst., 1981, Vol. 63, pages 59-82. Then the hydrophobic or lipophilic substance referred to is dispersed in the mixture, i.e. before or during the liposomic state. Then the lamellar liquid crystalline phase orients itself at the boundary zone between the oil phase or the lipophilic particles and the water phase. At cooling the lipids will crystallize as the chain length of the lipid is preferably selected so that the lipid will crystallize at a temperature between 100° C. and room temperature. When the crystallization takes place in said phase, the surface properties will be retained and in this way the crystals will be lipophilic against the encapsulated oil phase or the lipophilic particles and hydrophilic against the water phase.

In connection with liposomes it can also be added that different methods of preparing liposomes are of course previously known per se. Thus, DK 141082 discloses a novel method of preparing liposomes via so called liposome-precursors. Said method is based on the fact that the liposome-precursor is formed in a hydrophobic medium by means of lipids. These lipids are, however, in a lamellar liquid state. Moreover, WO 83/00294 discloses the use of lipids in liposome structures, but as the characterizing feature of a liposome is a liquid crystal layer this is also different from the present invention. Furthermore, these two references require the presence of additional substances such as bile salts, fatty acids and phospholipides which also give other structures than the one obtained by the present invention.

To obtain the best results in the process claimed the mixture is preferably kept at a temperature that exceeds said transition temperature with 5°-15° C., e.g. with 10° C., until equilibrium has been obtained. In this way one avoids for instance other liquid crystalline structures than the microscopic particles.

The temperature of the equilibrium mixture is then slowly lowered to the desired temperature, which is generally ambient temperature, a rapid stirring preferably being maintained to prevent the separation of a homogenous water phase within the mixture. However, the stirring rate should not be so high as to create a foaming effect. The temperature is preferably lowered at a rate of 0.5°-5° C. per minute until the crystallization takes place, after which the cooling rate is not critical.

As was mentioned above it has unexpectedly turned out in accordance with one aspect of the invention that lipopolar lipid crystals with the same structure as in water can be prepared also by means of some polar liquids, viz. glycerol, propylene glycol or ethylene glycol. This also represents an extremely valuable contribution to the prior art, as among advantages with a hydrophilic water-free medium there can be mentioned inter alia a reduced evaporation and no autoprotolyse. This type of crystal dispersion with or without encapsulated material is of a great value when it is desired to create a water-free cream product which is still easy to wash off.

In other words the invention also relates to a method of preparing polar lipid crystals without any encapsulation of hydrophobic or lipophilic substance, i.e. not any micro-capsules but instead a dispersion of the surface active crystals in the polar liquid. Said method corresponds to the process described above for the preparation of the micro-capsules with the exception that the step to incorporate the hydrophobic of lipophilic substance has been deleted which means that details as to the method can be taken from the above-mentioned disclosure. In general, however, this means that the method is characterized by mixing the polar lipid with a polar liquid having the ability of forming polar crystals of said polar lipid, such as glycerol, ethylene glycol or propylene glycol, to the formation of a mixture having a content of said polar liquid of 50-95 percent by weight, imparting to said mixture a temperature above the so called transition temperature for the lipid, which temperature is defined as the lowest temperature at which a particle of the lipid in contact with an excess of the polar liquid absorbs the same and is converted to cylindrical or spherical particles having a strong birefringence, maintaining said mixture above said temperature with stirring until the transformation has taken place and cooling the mixture with continued stirring to ambient temperature or the desired temperature, so that the polar solid crystals are formed.

As was the case in the manufacture of micro-capsules described above said mixture is preferably kept at a temperature which exceeds the transition temperature with 5°-15° until equilibrium has been reached.

Preferably the mixture is cooled at a rate of 0.5°-5° C. per minute.

The invention also relates to a crystal dispersion of the type that is obtainable by means of last-mentioned method. Said crystal dispersion is characterized in that it comprises a dispersion in the polar liquid of the polar lipid, that the polar liquid constitutes 50-95 percent by weight of the dispersion, and that the molecular orientation of the polar lipid in the crystal is such that the crystal surface essentially consists of polar end groups of the lipid, which inpart hydrophilic properties to the crystals.

As concerns other details in connection with the polar lipid and the polar liquid, respectively, reference is made to the above-mentioned details.

Finally, the invention relates to a completely novel use of micro-capsules, viz. in an ointment base. This opens up completely new possibilities of incorporating active substances into an ointment, as it has not been possible in practice to accomplish a product of said type by means of the previously known micro-capsules.

According to the present invention it has unexpectedly turned out that when spread on mucous membranes, e.g. skin areas, the encapsulated substance will come into contact with lipophilic receptor surfaces in such a way that the crystals will slide away and open a contact path for the encapsulated oil phase or any lipophilic particle.

The invention will now be described more specifically by means of working examples which relate to some preferable embodiments of the invention and which must not be considered limiting the same in other respects that what is claimed in the claims.

EXAMPLES

The lipid crystal-encapsulation has turned out to be an unexpectedly effective way of protecting oxidation-sensitive lipid substances. This can be utilized inter alia for food stuffs and medical preparations. Food stuffs enriched on essential fatty acid triglycerides, fat soluble vitamins and porfyrincomplexes of mineral substances represent the most important applications, but also spice oils and certain lipophilic flavouring agents can be protected in a similar way. This aspect of the invention is exemplified by Examples 1-7.

The planar chrystal structure means that the crystals possess light-reflecting properties, which in turn means that in accordance with the invention an improved stability can be imparted to light-sensitive substances. This is exemplified in Example 8.

By means of the lipid crystalline micro-encapsulating technique it is possible to alter or change surface properties of the substances present, which means that substances having adhesive, tacky properties are encapsulated and will become completely inert. This is requisite or necessary when the substance referred to belongs to the group of substances wich are hardly soluble in water and which have such a low melting point that problems are caused in use in for instance an ointment. Example 9 represents this case. In some cases it is desirable to perform the encapsulation in a water-free medium. This is exemplified in Example 10.

To obtain a higher melting point of the crystal shell and to obtain seeds for a re-crystallization after an occasional heating thereof the laurin- and myristin-monoglyceride can be partially or completely replaced by stearin- or palmitin-monoglycerides. This is exemplified by Example 11.

The invention can also be utilized to admix two or more components which are normally not compatible with each other. See Example 12.

Finally Example 13 shows the manufacture of a crystal dispersion of the polar lipid in another polar liquid but water.

As to the Examples it should be noted that all parts mentioned therein represent parts by weight.

EXAMPLE 1

28 parts of a mixture of laurin- and myristin-monoglyceride, 1+3, is mixed with 62 parts of water and heated to 70° C. Vitamin A, 10 parts, is added and the mixture is cooled to room temperature at a rate of 0.5° to 5° C. per minute. The vitamin stabilized in this way does not show any enhanced concentrations of degradation products in addition to what is disclosed in Ph. Eur. or USPXX after a storage at 20° C. for 2 years.

EXAMPLE 2

A mixture of 30 g of l-myristin monoglyceride is admixed with 95 g of water and heated to 65° C. At said temperature 5 g of alfa-tocopherol is added which is dispersed into the spherical aggregates of the lamellar liquid crystalline phase by means of ultra sound. This is most conveniently obtained by immersing an ultrasonic rod into the mixture. A period of from 10 to 20 minutes is generally sufficient for a non-detection of visible drops of alfa-tocopherol. The dispersion is then cooled in the same way as in Example 1. This water-dispersed form of alfa-tocopherol does not show any changes as to taste after having been stored at 20° C. for two years. Without giving any undesirable changes of taste it can be stirred into varying products such as for instance dressings, sauces, cream cheeses or keso.

EXAMPLE 3

To the hot (65° C.) monoglyceride-water mixture from Example 1 there are added 5 g of a marine oil enriched on polyunsaturated fatty acids within the range of $C_{20}$-$C_{26}$. The dispersion is cooled in accordance with Example 1. The product is considered having the effect of preventing the formation of thrombi.

EXAMPLE 4

To the hot (65° C.) monoglyceride-water mixture from Example 1 there are added 10 g of wheat-germ oil. Cooling is performed in accordance with Example 1. This product can replace gelatine-encapsulated wheat-germ oil.

EXAMPLE 5

To the hot monoglyceride-water mixture, 70°-80° C., from Example 1 one part of ditranole is added and cooling is performed in accordance with Example 1. This experiment is carried out in a nitrogen medium. In experiments concerning kept qualities this product keeps its quality for a longer time than commercial products.

EXAMPLE 6

Ditranol, 1 part, in Example 5 is replaced by Catechin, 2 parts. After 10 months the preparation is uncoloured while a conventional emulsion preparation is coloured by oxidated products already after 2 months.

EXAMPLE 7

Ascorbyl palmitate, 10 parts, are mixed with water, 88 parts, and heated to 75° C. After 15 minutes at said temperature with stirring 2 parts of ditranol are added and the temperature is lowered with 0.5°-5° C. per minute to 25° C. The micro-capsule manufactured in this way prevents a rapid oxidation of ditranol and is compatible with crystalline ointment bases based on the above-mentioned lipids.

EXAMPLE 8

1 monolaurin, 7 parts, are mixed with 1-monomyristin, 21 parts. Water, 74 parts, are added and after a heating to 70° C. oxytetracycline-dihydrate, 5 parts, are added. The mixture is cooled as was described earlier. Tetracycline present in the composition is stable against light-induced decomposition, which is illustrated by colour comparisons between the above-mentioned composition and a conventional ointment base containing tetracycline. After two months in sunlight the conventional composition is severely oxidized, the oxidation product being brown, while the above-mentioned composition is unchanged.

EXAMPLE 9

1-monolaurin is mixed with 1-myristin in a ratio of 30/70. Water, 70 parts, are mixed with 30 parts of monoglyceride mixture obtained above and with 5 parts of coal tar. The mixture is heated to 70° C. and is then cooled at a rate of 0.5°-5° C. per minute to room temperatur.

EXAMPLE 10

Water in Example 5 is replaced by glycerol. Otherwise the manufacturing conditions are the same. A water-free medium is an advantage as for instance oxygen or carbonate ions dissolved in the water can influence on the quality of the encapsulated substance..

EXAMPLE 11

10 parts of monolaurin, 10 parts of monostearin and 1 part of ditranol are mixed with 79 parts of water. After a heating to 75° C. the mixture is cooled to 30° C. at 0.5°-5° C. per minute.

EXAMPLE 12

7 parts of monomyristin and 21 parts of monolaurin are mixed with 1 part of ditranol and 71 parts of water. The mixture is heated to 70° C. and cooled to 40° C. at a rate of 0.5°-5° C. per minute. At 40° C. 30 percent hydrogen peroxide, 6.7 parts, are added and cooling is continued to 30° C. Ditranol can be replaced by for instance Catechin, Xylocain, Prednisolon or Inositol-Niacinat. By the encapsulation in lipid crystals the oxidation-sensitive substances will be compatible with hydrogen peroxide.

EXAMPLE 13

Glycerol, 90 parts, are mixed with monolaurin, 3 parts, and monomyristin, 7 parts. The mixture is heated to 70° C. and after stirring for 15 minutes it is cooled to room temperature at a rate of 0.5°–5° C. The end product is a cream that can be used to prevent the penetration of solvent vapours through the skin.

We claim:

1. A micro-capsule composition consisting essentially of a hydrophobic or lipophilic substance surrounded by surface-active solid crystals of polar lipids, which crystals have a hydrophilic side that is exposed outwards and a hydrophobic side that is turned inwards toward the hydrophobic or lipophilic substance.

2. The micro-capsule composition of claim 1, wherein the lipid has a crystallization temperature of between about 20° C. and about 100° C.

3. The micro-capsule composition of claim 1, wherein the hydrophobic or lipophilic substance is coal-tar.

4. The micro-capsule composition of claim 1, wherein the hydrophobic or lipophilic substance is selected from the group consisting of marine oils, ditranol, vitamin A, vitamin D and flavonoides.

5. The micro-capsule composition of claim 4, wherein the flavonides are selected from the group consisting of catechin, rutin, rotenon, pyretrum and tannin.

6. The micro-capsule composition of claim 1 wherein the hydrophobic or lipophilic substance is tetracycline.

7. The micro-capsule composition of claim 1, wherein the hydrophobic or lipophilic substance constitutes greater than zero and up to about 90 percent by weight of the micro-capsule.

8. The micro-capsule composition of claim 1 consisting essentially of a dispersion of the micro-capsules in water or any other polar liquid having the ability of forming surface-active solid crystals from polar lipids, the polar liquid constituting from about 50 to 95 percent by weight of the dispersion, and the surface-active crystals constituting from about 5 to 50 percent by weight of the dispersion.

9. The micro-capsule composition of claim 8, wherein the micro-capsules are dispersed is water.

10. The micro-capsule composition of claim 8, wherein the proportion of hydrophobic or lipophilic substance is from about 0.1 to 15 percent by weight of the composition.

11. The micro-capsule composition of claim 1 in an ointment base.

12. The micro-capsule composition of claim 1, wherein the lipid crystals are $\beta$-crystals of a lipid selected from the group consisting of monoglycerides of fatty acids, ascorbic acid esters of fatty acids, phosphate esters of fatty acids, lactic acid esters of fatty acids and monoglycerol ethers.

13. The micro-capsule composition of claim 12, wherein the fatty acids and the ether chains have 12 to 18 carbon atoms.

14. The micro-capsule composition of claim 12, wherein the monoglyceride is selected from the group consisting of 1-monolaurin, 1-monomyristin, 1-monopalmitin and 1-monostearin.

15. The micro-capsule composition of claim 12, wherein the monoglyceride is a mixture of two or more of the monoglycerides.

16. The micro-capsule composition of claim 15, wherein the mixture is 1-monolaurin and 1-monomyristin such that the proportion of 1-monolaurin is at least 10 percent by weight.

17. The micro-capsule composition of claim 12, wherein the fatty acids and the ether chains are saturated.

18. A crystal dispersion of a polar lipid in a polar liquid other than water, wherein the dispersion consists essentially of a dispersion of the polar lipid in a polar liquid other than water and having the ability of forming polar solid crystals of the polar lipid where the polar liquid constitutes from about 50 to 95 percent by weight of the dispersion, and where the molecular orientation of the polar lipid within the crystal is such that the crystal surface consists essentially of polar end groups of the lipid, which impart hydrophilic properties to said crystals.

19. The crystal dispersion of claim 18, wherein the polar liquid is selected from the group consisting of glycerol, ethylene glycol and propylene glycol.

* * * * *